United States Patent [19]

Kim et al.

[11] Patent Number: 5,516,926
[45] Date of Patent: May 14, 1996

[54] (+)2-BENZOYL-3-(SILYLOXYPROP-2(S)-YL)AMINOACRYLATE DERIVATIVES AND A METHOD FOR PREPARING THE SAME

[75] Inventors: Youseung Kim; Soon Bang Kang; Seonhee Park, all of Seoul, Rep. of Korea

[73] Assignee: Korea Institute of Science and Technology, Seoul, Rep. of Korea

[21] Appl. No.: 452,167

[22] Filed: May 26, 1995

[30] Foreign Application Priority Data

May 28, 1994 [KR] Rep. of Korea ............... 11748/1994

[51] Int. Cl.⁶ ..................................................... C07F 7/10
[52] U.S. Cl. ..................................................... 556/418
[58] Field of Search .............................................. 556/418

[56] References Cited

U.S. PATENT DOCUMENTS

| | | | |
|---|---|---|---|
| 3,258,477 | 6/1966 | Plueddemann et al. | 556/418 |
| 3,398,210 | 8/1968 | Plueddemann et al. | 556/418 X |
| 4,845,257 | 7/1989 | Naito et al. | 556/418 |
| 4,892,961 | 1/1990 | Terashima et al. | 556/418 X |
| 5,389,619 | 2/1995 | Doetzer et al. | 556/418 X |

*Primary Examiner*—Paul F. Shaver
*Attorney, Agent, or Firm*—Townsend and Townsend and Crew

[57] ABSTRACT

(+)2-benzoyl-3-(silyloxyprop-2(S)-yl)aminoacrylate derivative of following formula I which can be an useful starting material for producing a potent antibacterial compound and a method for the preparation of the same:

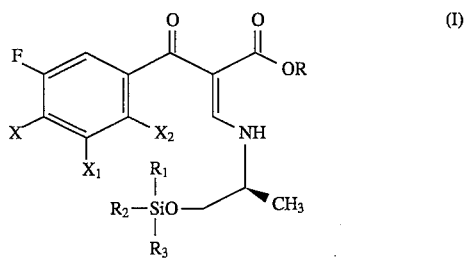

wherein X is fluoro or chloro; $X_1$ and $X_2$ can be halogen or nitro; and R, $R_1$, $R_2$ and $R_3$ each can be $C_{1-8}$ alkyl group.

8 Claims, No Drawings

(+)2-BENZOYL-3-(SILYLOXYPROP-2(S)-YL)AMINOACRYLATE DERIVATIVES AND A METHOD FOR PREPARING THE SAME

BACKGROUND OF THE INVENTION

1. Field of the Invention

The present invention relates to novel compounds useful for synthesizing antibacterially active piperazine benzoxazine derivatives. More particularly, the present invention is concerned with (+)2-benzoyl-3-(silyloxyprop-2(S)-yl)amino acrylate derivatives and a preparing method thereof.

2. Description of the Conventional Art

Intermediates for synthesis of (−)piperazine benzoxazine derivatives and preparing methods thereof are disclosed in German Patent No. 3,543,513; Chemical Abstract 107, 154342c (1987); L. A. Mitscher et al., J. Med. Chem., 30, 2283 (1987)).

German Patent No. 3,543,513 (1987) and Chemical Abstract 107, 154342c (1987) relate to compounds of the type

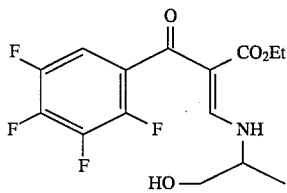

and a preparing method thereof. However, the preparation method comprising reacting ethyl ethoxymagnesium malonate with 2,3,4,5-tetrafluorobenzoyl chloride to give ethyl(2,3,4,5-tetrafluorobenzoyl)acetate, reacting the ethyl(2,3,4,5-tetrafluorobenzoyl)acetate with triethyl orthoformate and acetic anhydride, and substituting with 2-amino-1-propanol, is complicated and the product yield is relatively low.

DESCRIPTION OF THE INVENTION

The present invention relates to novel compounds useful to synthesize antibacterially active compound. More particularly, the present invention is concerned with (+)2-benzoyl-3-(silyloxyprop-2(S)-yl)amino acrylate derivatives having the following formula I:

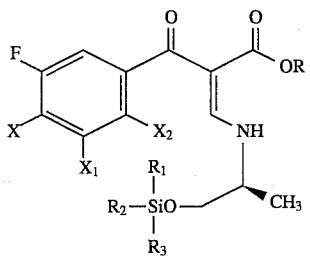

wherein X is fluoro or chloro; $X_1$ and $X_2$ can be halogen or nitro; and R, $R_1$, $R_2$, and $R_3$ each can be $C_{1-8}$ alkyl group.

This compound can be used as a starting material for synthesizing pyrido benzoxazine derivatives of the following general formula II which in turn serve as a useful intermediates for synthesizing potent antibacterial piperazine benzoxazine derivatives, especially, (−)9-fluoro-7-oxo-2,3-dihydro-7H-pyrido[1,2,3-de]-1,4-benzoxazine-6-carboxylicacid derivatives.

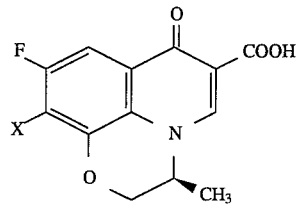

wherein X is fluoro or chloro.

The preparation method of the compound of formula it is described in detail in Korean Patent Application No. 11460/94 of the present inventors, filed on May 26, 1994.

The present invention is also concerned with a method for the preparation of (+)2-benzoyl-3-(silyloxyprop-2(S)-yl)amino acrylate derivatives of formula I.

The compounds of formula I can be obtained by reacting acrylate of the following formula III.

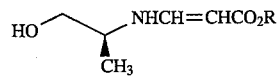

wherein R is $C_{1-8}$ alkyl group, with a silyl compound of following formula IV

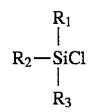

wherein $R_1$, $R_2$ and $R_3$ can be $C_{1-8}$ alkyl group, in an organic solvent in the presence of a suitable base, to give (+) silyloxyacrylate of the following formula V

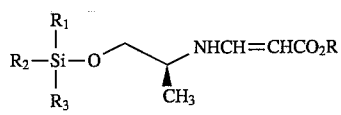

wherein R, $R_1$, $R_2$ and $R_3$ each can be a $C_{1-8}$ alkyl group;

treating (+) silyloxyacrylate of formula V with benzoyl chloride of the following formula VI

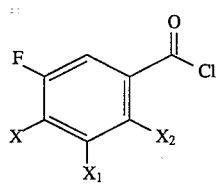

wherein X is fluoro or chloro; $X_1$ and $X_2$ can be halogen or nitro, in an organic solvent in the presence of a suitable base to obtain (+)2-benzoyl-3-(silyloxyprop-2(S)-yl)aminoacrylate derivatives of formula I.

The preparation method of acrylate derivatives of formula III is described in detail in the Korean Patent Application No. 5761/1994 of the present inventors, filed Mar. 22, 1994.

In order to help understand the present invention, the preparation method of the present invention is summarized in the following scheme.

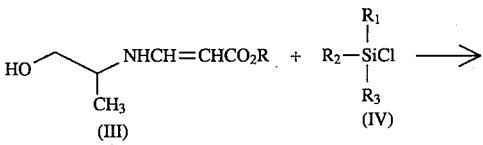

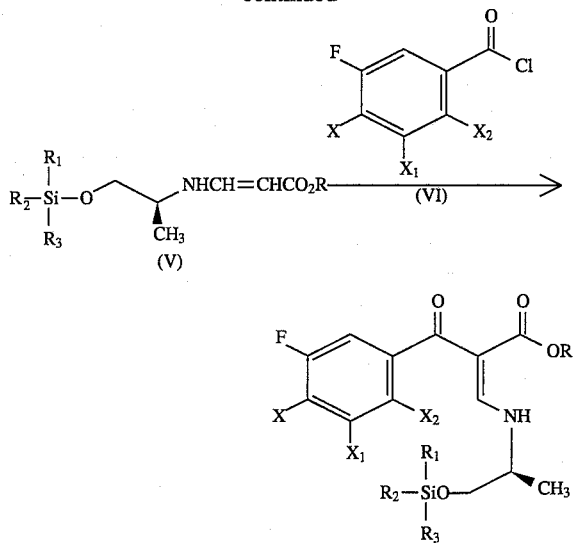

In accordance with a further aspect of the present invention, a novel compound of formula V, an intermediate useful to prepare the compound of formula I is also provided.

The organic solvent effective for the reaction of an acrylate of formula III with trialkylsilylchloride of formula IV includes dimethylformamide, tetrahydrofuran, methylene chloride, acetonitrile, benzene, or toluene. In the organic solvent, this reaction is carried out at a temperature of 0° to 30° C. for 1 to 24 hours in the presence of a base such as pyridine, triethylamine, 2,6-lutidine, 4-dimethylamino pyridine, imidazole, 1,8-diazabicyclo[5.4.0]undec-7-ene, or 1,5-diazabicyclo[4.3.0]non-5-ene to give a novel (+) silyl oxyacrylate of formula (V). In the reaction, the equivalent ratio of the compound of formula III to the compound of formula IV to the base compound is preferably 1:1.1:1.2 to 1:1.2:1.5.

Then in an organic solvent, such as methylenechloride, acetonitrile, diethylether, ethylenechloride, dimethyl formamide, tetrahydrofuran, or chloroform, silyloxyacrylate of formula V is reacted with benzoylchloride of formula VI at a temperature of 0° to 100° C. for 30 minutes to 10 hours in the presence of a suitable base such as triethylamine, pyridine, 4-dimethylaminopyridine, imidazole, 2,6-lutidine, 1,8-diazabicyclo[5.4.0]undec-7-ene, 1,5-diazabicyclo[4.3.0]non-5-ene, so as to give a (+)2-benzoyl-3-(silyloxypropy-2(S)-yl)amino acrylate derivative of formula I, a novel compound. In this reaction, the equivalent ratio of the compound of formula V to the compound of formula VI to the base is preferably in the range of 1:1.05:1.1 to 1:1.1.:1.2.

The products of those reactions can be separated and purified by conventional techniques, such as evaporation, filtration, extraction, chromatography, distillation and combinations thereof. For example, the mixture containing the product is condensed under reduced pressure to dry it. The resultant residue is mixed with a mixture of water and an organic solvent, such as methylene chloride, chloroform, diethylether or ethylacetate, and then the organic solvent is condensed to give a product. In case of a mixture of the product and by-products, further purification may be performed by chromatography, re-distillation or recrystallization.

The preferred embodiments of the present invention will now be further described with reference to specific examples. Variations and modifications of these embodiments can be effected without departing from the spirit and scope of the invention as described and claimed.

Unless otherwise stated, all percentages, parts and ratios therein are by weight.

A. Preparation of Intermediates

Example 1

(+)Ethyl 3-(1-t-butyldimethylsilyloxyprop-2(S)-yl)aminoacrylate(V: R=ethyl, $R_1$, $R_2$=methyl, $R_3$=t-butyl)

3.35 g (22 mmol) of t-butyldimethylsilylchloride (IV, $R_1$, $R_2$=methyl, $R_3$=t-butyl) and 3.65 g (24 mmol) of 1,8-diazabicyclo[5.4.0]undec-7-ene were added to 40 ml of benzene and cooled to 5° C. To this, 3.46 g (20 mmol) of (+) ethyl 3-(1-hydroxyprop-2(S)-yl)aminoacrylate (III, R=ethyl) dissolved in 10 ml of benzene was slowly added dropwise. The reaction mixture was stirred at a room temperature for about 16 hours. The precipitate was removed by filtration. The filtrate was washed sequentially with 5 ml of 0.2N aqueous hydrochloric acid solution, 5 ml of saturated aqueous solution of sodium bicarbonate, 5 ml of saturated saline water and dried over magnesium sulfate.

Thereafter, the solvent was removed under reduced pressure (25° C./20 mmHg), to give 5.63 g of a colorless oily product (yield 98%).

Analysis of the product revealed that Z and E isomers were precent in a ratio of 3:2 therein.

B.P.: 80°–90° C./1.6 mmHg $[\alpha]^{20}_D$: +109.8° C. (C=2.806, $CHCl_3$)

IR (NaCl) $cm^{-1}$: 3320, 2955, 2930, 2987, 2858, 1668, 1616, 1473

NMR($CDCl_3$) ppm: 7.68–7.85(1H×0.74, m), 7.48(1H× 0.24, dd, J=13.2H, 9.5H), 6.71(1H×0.76, dd, J=13.2H, 8H), 4.74(1H×0.24, d, 13.2H), 4.63–4.73(1H×0.24, m), 4.44(1H× 0.76, d, J=8H), 4.10(2H, q, J=7.1H), 3.43–3.65(2H, m), 3.23–3.32m(1H, m), 1.27(3H, t, J=7.1H), 1.18(3H, d, J=6.6H), 0.89(9H, s), 0.037(6H, s).

Example 2

(+)Ethyl 3-(1-t-butyldimethylsilyloxyprop-2(S)-yl) aminoacrylate (V: R=ethyl, $R_1$, $R_2$=methyl, $R_3$=t-butyl)

1.82 g (10.5 mmol) of (+)ethyl 3-(1-hydoxyprop-2(S)-yl)aminoacrylate (III, R=ethyl) and 1.74 g (11.6 mmol) of t-buthyldimethylsilyl chloride (IV, $R_1$, $R_2$=methyl, $R_3$=t-butyl) were added to 50 ml of tetrahydrofuran. To this solution, 0.86 g (12.6 mmol) of imidazole was slowly added and stirred for 8 hours at the temperature of 25° C. Then, the reaction solvent was removed under a reduced pressure (25° C./20 mm Hg) and added with 50 ml of methylenechloride.

Thereafter, the reaction mixture was washed with 5 ml of aqueous 0.1N hydrochloric acid solution, 5 ml of saturated aqueous sodium bicarbonate solution, and 5 ml of saturated saline water, in due order and then dried over magnesium sulfate. The organic solvent was completely removed under reduced pressure (20° C./10 mm Hg), to give 2.74 g of an oily product (yield 94%).

Example 3

(+)Ethyl 3-(1-t-butyldimethylsilyloxyprop-2(S)-yl)aminoacrylate(V: R=ethyl, $R_1$, $R_2$=methyl, $R_3$=t-butyl)

2.32 g (13.4 mmol) of (+)ethyl 3-(1-hydroxyprop-2(S)-yl)aminoacrylate (III, R=ethyl) and 2.22 g (14.8 mmol)of t-butyldimethylsilychloride (IV, $R_1$, $R_2$=methyl, $R_3$=t-butyl)

were added to 50 ml of dimethylformamide. To this solution, 1.27 g (16.1 mmol) of pyridine was slowly added dropwise and stirred for 10 hours at the temperature of 25° C. Then, the reaction mixture was purified as described in Example 2 so as to give 3.38 g of an oily product (yield 91%).

B. Preparation of the Product

Example 4

(+)Ethyl 2-(2,3,4,5-tetrafluoro)benzoyl-3-(1-t-butyldimethylsilyloxyprop-2(S)-yl)aminoacrylate (I: X, $X_1$, $X_2$=fluoro, R=ethyl, $R_1$, $R_2$=methyl, $R_3$=t-butyl)

2.66 g (9.26 mmol) of (+)ethyl 3-(1-t-buthyldimethylsilyl oxyprop-2(S)-yl)aminoacrylate (V; R=ethyl, $R_1$, $R_2$=methyl, $R_3$-t-butyl) and 1.03 g (10.2 mmol) of triethylamine were added to 70 ml of acetonitrile. To this solution, 2.06 g (9.7 mmol) of 2,3,4,5-tetrafluorobenzoyl chloride (VI, X, $X_1$, $X_2$=fluoro) was slowly added dropwise. The reaction mixture was stirred for 10 hours.

Thereafter, the organic solvent was removed under reduced pressure (25° C./10 mmHg), to leave the residue which was subsequently added with 100 ml of methylenechloride. The reaction mixture was washed with 10 ml of aqueous saturated ammonium chloride solution, 10 ml of aqueous saturated sodium bicarbonate solution and 10 ml of saturated saline water, in due order.

The solvent was dried over magnesium sulfate and removed completely under reduced pressure (25° C./20 mmHg), to give 4.26 g of an oily product (yield 99%).

Analysis of the product revealed that the product is an isomeric mixture containing cis and trans isomers were present in a ratio of 7:3 or 3:7 therein.

IR (NaCl) cm$^{-1}$: 3230, 2955, 2933, 2901, 2858, 1701, 1630, 1570, 1523, 1481

$[\alpha]^{19}_D$: +71.6° C. (C=1.32, CHCl$_3$)

NMR(CDCl$_3$) ppm: 10.75–10.91(1H×7/10, m), 9.45–9.58(1H×3/10, m), 8.18 (1H, d, J=14.2H), 7.03–7.14(1H×3/10, m), 6.91–7.00(1H×7/10, m), 3.97 and 4.06(2H, each q, J=7H), 3.48–3.76(3H, m), 1.13(3H, d, J=6.5H), 1.12(2H, t, J=7H), 0.89(9H, s), 0.06(6H, d, J=3.9H)

Example 5

(+)Ethyl 2-(2,3,4,5-tetrafluoro)benzoyl-3-(1-t-butyldimethylsilyloxyprop-2(S)-yl)aminoacrylate (I: X, $X_1$, $X_2$=fluoro, R=ethyl, $R_1$, $R_2$=methyl, $R_3$=t-butyl)

2.10 g (7.32 mmol) of (+)ethyl 3-(1-t-butyldimethylsilyloxyprop-2(S)-yl)aminoacrylate (V; R=ethyl, $R_1$, $R_2$=methyl, $R_3$=t-butyl) and 0.64 g (8.05 mmol) of pyridine were added in 50 ml of tetrahydrofuran. To this solution, 1.63 g (7.69 mmol) of 2,3,4,5-tetrafluorobenzoyl chloride (VI, X, $X_1$, $X_2$=fluoro) was added. The mixture was heated for 3 hours with stirring.

The reaction mixture was purified as described in Example 4 to give 3.22 g of an oily product (yield 95%).

Example 6

(+)Ethyl 2-(2,3,4,5-tetrafluoro)benzoyl-3-(1-t-butyldimethylsilyloxyprop-2(S)-yl)aminoacrylate (I: X, $X_1$, $X_2$=fluoro, R=ethyl, $R_1$, $R_2$=methyl, $R_3$=t-butyl)

1.35 g (4.7 mmol) of (+)ethyl 3-(1-t-butyldimethyl silyloxyprop-2(S)-yl)aminoacrylate (V; R=ethyl, $R_1$, $R_2$=methyl, $R_3$=t-butyl) and 0.38 g (5.64 mmol) of imidazole were added to 50 ml of acetonitrile. To this solution, 1.1 g (5.2 mmol) of 2,3,4,5-tetrafluorobenzoyl chloride (VI, X, $X_1$, $X_2$=fluoro) was added. The mixture was heated for 4 hours with stirring.

The reaction mixture was purified as described in Example 4 to give 2.03 g of an oily product (yield 93%).

Example 7

(+)Ethyl-2-(2-nitro-3,4,5-trifluoro)benzoyl-3-(1-t-butyldimethylsilyloxyprop-2(S)-yl)aminoacrylate (I: X, $X_1$,=fluoro, $X_2$=nitro, R=ethyl, $R_1$, $R_2$=methyl, $R_3$=t-butyl)

2.3 g (8 mmol) of (+)ethyl 3-(1-t-butyldimethylsilyl oxyprop-2(S)-yl)aminoacrylate (V; R=ethyl, $R_1$, $R_2$=methyl, $R_3$=t-butyl) and 0.89 g (8.8 mmol) of triethylamine were added to 100 ml of acetonitrile and cooled to 0° C. To this solution, 2.01 g (8.4 mmol) of 2-nitro-3,4,5-trifluorobenzoyl chloride (VI, X, $X_1$=fluoro, $X_2$=nitro) was slowly added dropwise and stirred at room temperature for 3 hours. The precipitate was filtered off and filtrate was concentrated under reduced pressure (25° C./20 mmHg), to leave the residue which was subsequently added with 50 ml of methylenechloride. The reaction mixture was washed with 10 ml of aqueous saturated ammonium chloride solution, 10 ml of aqueous saturated sodium bicarbonate solution and 10 ml of saturated saline water, in due order and dried over magnesium sulfate. The solvent was removed completely under reduced pressure (25° C./20 mmHg), to give 3.8 g of an oily product (yield 98%).

Analysis of the product revealed that the product is an isomeric mixture containing cis and trans isomers were present in a ratio of 4:1 or 1:4 therein.

IR (NaCl) cm$^{-1}$: 2951, 1695, 1630, 1550

$[\alpha]^{19}_{589}$: +58.0° C. (C=2.0, CHCl$_3$)

$^1$H-NMR (CDCl$_3$) ppm: 9.60–9.73 and 10.71–10.89 (1H, each br), 8.31 (1H×1/5 , d, J=15H), 8.20 (1H×4/5 , d, J=14.3H), 6.86–6.92 (1H, m), 3.96 and 4.02 (2H, each q, J=7.1H), 3.50–3.78 (3H, m), 1.35 (3H, d, J=6.4H, 1.13 (3H, t, J=7.1H), 0.90 (9H, s), 0.07 (6H, d, J=3H).

What is claimed is:

1. A (+)2-benzoyl-3-(silyloxyprop-2(S)-yl)aminoacrylate derivative having formula I:

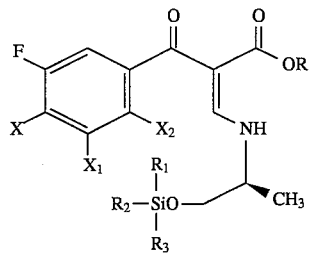

wherein X is fluoro or chloro; $X_1$ and $X_2$ can be halogen or nitro; and R, $R_1$, $R_2$, and $R_3$ each can be $C_{1-8}$ alkyl group.

2. A (+) silyloxyacrylate derivative having formula V:

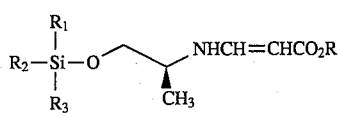

wherein R, $R_1$, $R_2$, and $R_3$ each can be $C_{1-8}$ alkyl group.

3. A method for preparing a (+)silyloxyacrylate derivative of formula V which comprises reacting (+) acrylate derivative of formula III with trialkylsilylchloride of formula IV in organic solvent at a temperature of 0° to 30° C. for 1 hour to 24 hours in the presence of a base:

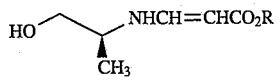

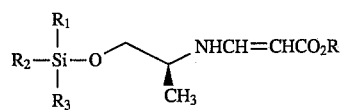

wherein R, $R_1$, $R_2$, and $R_3$ can be $C_{1-8}$ alkyl group.

4. The method according to claim 3, wherein the organic solvent is selected from the group consisting of dimethylformamide, acetonitrile, tetrahydrofuran, methylene chloride, benzene, toluene, ethylether.

5. The method according to claim 3, wherein the base is selected from the group consisting of pyridine, triethylamine, imidazole, 2,6-lutidine, 1,8-diazabicyclo[5.4.0]undec-7-ene, and 1,5-diazabicyclo[4.3.0]non-5-ene.

6. A method for producing (+)2-benzoyl-3-(silyloxyprop-2(S)-yl) aminoacrylate derivative of the following formula I which comprises reacting (+)silyloxyacrylate derivative of formula (V) with benzoylchloride derivative of formula (VI) in organic solvent at a temperature of 0° to 100° C. for 30 minutes organic solvent at a temperature of 0° to 100° C. for 30 minutes to 12 hours in the presence of a base:

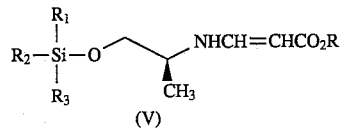

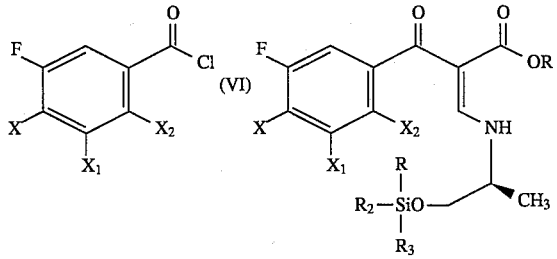

wherein X is fluoro or chloro; $X_1$ and $X_2$ can be halogen or nitro; R, $R_1$, $R_2$, and $R_3$ each can be $C_{1-8}$ alkyl group.

7. The method set forth in claim 6, wherein said base is selected from a group consisting of triethylamine, pyridine, 4-dimethylaminopyridine, imidazole, 2,6-lutidine, 1,8-diazabicyclo[5.4.0]undec-7-ene and 1,5-diazabicyclo[4.3.0]non-5-ene.

8. The method set forth in claim 6, wherein said organic solvent is selected from a group consisting of methylene chloride, acetonitrile, diethylether, dimethyl formamide, tetrahydrofuran, and chloroform.

* * * * *